United States Patent [19]

Evans

[11] Patent Number: 4,684,610
[45] Date of Patent: Aug. 4, 1987

[54] PROCESS FOR CONVERTING 1,2-SATURATED STEROIDS TO 1,2-DEHYDRO STEROIDS

[75] Inventor: Timothy W. Evans, Park Township, Three Rivers County, Mich.

[73] Assignee: The Upjohn Company, Kalamazoo, Mich.

[21] Appl. No.: 724,036

[22] Filed: Apr. 17, 1985

Related U.S. Application Data

[63] Continuation of Ser. No. 475,437, Mar. 15, 1983, abandoned.

[51] Int. Cl.$^4$ .............................................. C12P 33/02
[52] U.S. Cl. ...................................................... 435/61
[58] Field of Search .......................................... 435/61

[56] References Cited

U.S. PATENT DOCUMENTS

| | | | |
|---|---|---|---|
| 2,837,464 | 6/1958 | Nobile | 195/51 |
| 3,360,439 | 12/1967 | Erickson et al. | 435/61 |
| 3,718,542 | 2/1973 | Irmscher et al. | 435/61 |
| 4,035,236 | 7/1977 | Wovcha | 195/51 |
| 4,041,055 | 8/1977 | Shephard et al. | 260/397.3 |

OTHER PUBLICATIONS

Yamane et al., Biotechnology and Bioengineering, vol. XXI, pp. 2133-2145 (1979).
Sonomoto et al., Agric. Biol. Chem., vol. 44(5), pp. 1119-1126 (1980).
Sonomoto et al., European J. Appl. Microbiol Biotechnol., vol. 6, pp. 325-334 (1979).
Charney, W. et al., Microbial Transformation of Steroids, 1967, pp. 4-9.
Charney, W. et al., Microbial Transformation of Steroids, 1967, pp. 236-261.

*Primary Examiner*—Alvin E. Tanenholtz
*Attorney, Agent, or Firm*—Roman Saliwanchik; Bruce Stein

[57] ABSTRACT

Disclosed and claimed is an improved microbial bioconversion to produce 1,2-dehydro steroids from their corresponding 1,2-saturated derivatives by use of a water-immiscible solvent comprising an aromatic hydrocarbon in the reaction procedure.

9 Claims, No Drawings

PROCESS FOR CONVERTING 1,2-SATURATED STEROIDS TO 1,2-DEHYDRO STEROIDS

This is a continuation of Ser. No. 475,437 filed Mar. 15, 1983 and now abandoned.

BACKGROUND OF THE INVENTION

The first therapeutic use of corticosteroids was demonstrated in the 1950's with the introduction of cortisone acetate treatment for rheumatoid arthritis. Further studies demonstrated that the insertion of unsaturation into the 1,2 position of hydrocortisone and cortisone caused the resultant steroids, prednisolone and prednisone, to have enhanced potency and to cause less drug-induced salt retention. Subsequently, most other steroids used for the treatment of corticoid-responsive diseases have been synthesized so that they contain a double bond in the 1,2 position of the steroid molecule. In 1977, two U.S. patents were issued which represent new approaches to the synthesis of corticosteroids from sterol precursors. U.S. Pat. No. 4,035,236 covers a process for preparing 9α-hydroxyandrostenedione via fermentation of sitosterol, stigmasterol, or cholesterol. U.S. Pat. No. 4,041,055 discloses a general process for the synthesis of medically useful corticosteroids from this androstene. Intermediates covered in this chemistry can possess a 3-keto-$\Delta^{4,9(11)}$ configuration.

Following are prior art methods which disclose the bioconversion of 1,2-saturated steroids to their corresponding 1,2-dehydro steroids:

(A) U.S. Pat. No. 2,837,464 "Process for Production of Dienes by *Corynebacterium*"

Description of 1-dehydrogenation of steroids in fermentation beers by *Arthrobacter (Corynebacterium) simplex*.

(B) U.S. Pat. No 3,360,439 entitled "Process for Preparing 1-dehydro Steroids".

Description of 1-dehydrogenation of steroids by use of *A. simplex* cells pretreated with a lower alkanol or lower alkanone such as acetone before mixing with the substrate and a hydrogen carrier.

(C) Charney, W. and Herzog, H. 1967. *Microbial Transformation of Steroids*. Academic Press, Inc., New York, pp 4–9, 236–261.

Historical background on steroid bioconversions and taxonomic listing of microorganisms known to carry out 1-dehydrogenation.

(D) T. Yamane, H. Nakatani, E. Sada, T. Omata, A. Tanaka and S. Fukui, *Biotechnology and Bioengineering*, 21. 1979.

The authors studied the $\Delta^1$-dehydrogenation of 4-androstene-3,17 dione with *Nocardia rhodocrous.*

They used 50% benzene-heptane as a solvent. They report that the advantage of using the solvent is that it increases the reaction rate by a factor of 180. (Benzene is a human carcinogen).

It should be noted that this enzyme must be different than that produced by *A. simplex*. The *Nocardia rhodocrous* enzyme is not active in the presence of menadione, the electron acceptor of choice for *A. simplex*.

The preferred electron acceptor for the *Nocardi rhodocrous* is phenazine methosulfate. This electron acceptor is too expensive and unstable to render this microbial activity practical.

They have also run the reaction with the solvent only 20% saturated with the steroid. They demonstrate that increasing the concentration of the steroid decreases the reaction rate.

The solvent 50% benzene-heptane is flammable in the presence of oxygen. Oxygen is an essential reagent of the reaction. The authors did not discuss how oxygen could be introduced without producing an explosive environment in the reactor.

(E) K. Sonomoto, I. Jin, A. Tanaka and S. Fukui; *Agric. Biol. Chem.*, 44, 1119–1126, 1980.

The same lab studied the $\Delta^1$-dehydrogenation of hydrocortisone with *A. simplex*. They considered two immiscible solvents, n-butanol and n-amyl alcohol, and reported that the reaction did not proceed in the presence of these solvents. They preferred water miscible solvents and chose 10% methanol-water and 10% propylene glycol-water as their solvents.

BRIEF SUMMARY OF THE INVENTION

An improved process for $\Delta^1$-dehydrogenating steroids with *A. simplex*. This process involves the addition of an aromatic hydrocarbon as a water immiscible solvent to an aqueous slurry of *A. simplex* cells, an exogenous electron acceptor and the steroid to be $\Delta^1$-dehydrogenated. The slurry is agitated and oxygen is made available such that the oxygen content in the gas space is less than the minimum oxygen for combustion; or the reaction is performed below the flash point of the organic solvent.

This procedure is superior to the prior art technology for steroid $\Delta^1$-dehydrogenation with *A. simplex* because of the following:

a. lower unconverted starting steroid levels are obtainable;

b. this process can be run at higher steroid concentrations;

c. less *A. simplex* cells are required to convert a given quantity of steroid; and d. this process is more tolerant of organic soluble impurities present in the steroid, *A. simplex* cells or produced from the steroid by the cells.

Further, this procedure is superior to prior technology for steroid $\Delta^1$-dehydrogenations with other microbial activities such as *Nocardia rhodocrous* because the *A. simplex* catalyzed reaction can be performed with inexpensive and stable electron acceptors such as menadione.

DETAILED DESCRIPTION OF THE INVENTION

The process of the subject invention can be practiced as shown by the following examples which should not be construed as limiting:

EXAMPLE 1

(1) Combine in a reaction vessel (1 l basis)
  (a) 0.9 l of 50 mM $KPO_4$ buffer, pH=7.5
  (b) 3.66 gm of dry *A. simplex* cells
  (c) 0.08 gm of menadione
  (d) 8 gm of 21-acetoxy-pregn-4,9(11),16-triene-3,20 dione
  (e) 100 ml of toluene.

(2) Agitate at 15 cal/l. min.

(3) Add air as necessary to maintain oxygen in the gas space of the reaction vessel at about 3 to 6%.

(4) Maintain temperature at 28° C.∓1° C.

(5) After 25 hrs. collect the toluene phase.

For this example the steroid in the toluene phase was 94.3% 21-acetoxy-pregn-1,4,9(11), 16-tetraene-3,20-dione 4.2% 21-hydroxy-pregn-1,4,9(11), 16-tetraene-3,20-dione 1.5% 21-acetoxy-pregn-4,9(11), 16-triene-3,20-dione The following range of variables can be used for the above steps:

(Step 1)

(a) Buffer pH can be in the range 6 to 10.

(b) Quantity of A. simplex is reduced to a level just sufficient to push the reaction to completion. Typical levels are 0.05 to 1.0 gm per gm of steroid. The microbial source of the enzyme; Arthrobacter (Corynebacterium) simplex (ATCC 6946) or Bacterium cyclooxydans (ATCC 12673).

Preparation of the microorganism: The A. simplex cells may be used in the fermentation broth or modified by collecting the cells, drying, acetone treatment or immobilization, by methods well known in the art.

(c) The electron acceptor can be selected from the following: Menadione (2-methyl-1,4 naphthoquinone), Menadione bisulfite, 1,4 naphthoquinone and other vitamin K-type compounds.

The level of the electron acceptor is determined by cost and reaction rate considerations. The reaction rate is linearly proportional to the menadione concentration. Typical levels are about 5 to about 40 gm/kg of steroid.

(d) Steroid concentration should be as high as possible, so long as there is efficient conversion.

The steroid would belong to the 3-keto-$\Delta^4$-androstene or the 3-keto-$\Delta^4$-pregnene series and preferably should have a solubility in the organic solvent of greater than 5 g/liter.

(e) The aromatic hydrocarbon can be chosen from toluene, benzene or xylene. These solvents may be used together or diluted with another water immiscible solvent such as heptane, or methylene chloride.

The quantity of aromatic hydrocarbon can range from about one-half of that necessary to dissolve the most soluble of the starting steroid or the product steroid to about 4 times that necessary to dissolve the least soluble of the starting steroid or the product steroid.

For this example toluene was added at a level just sufficient to dissolve the steroid at the completion of the reaction.

The aromatic hydrocarbon is preferably added with the steroid. However, the aromatic hydrocarbon may be added at later times or earlier times.

(Step 2)

Agitate at as high agitation power as possible. The reaction rate is a strong function of the agitation power.

(Step 3)

The reaction requires oxygen as the final hydrogen (electron and proton) acceptor. However, due to the presence of the aromatic hydrocarbon, an explosive environment will exist in the gas space of the reactor. To overcome this hazard the oxygen concentration in the gas space is, advantageously, maintained well below the minimum oxygen for combustion. For benzene the minimum oxygen is 11.2%. For the xylene's it is also possible to perform the reaction below the flash point. The flash point for m-xylene, o-xylene and p-xylene are 29, 32 and 39° C., respectively.

(Step 4)

The temperature of the reaction can be from about 0 to about 45° C.

(Step 5)

The reaction is typically run for 2 days. It could be run for a few hours to a few weeks.

EXAMPLE 2

Comparison of Toluene and Aqueous Procedures (A) Procedure:

Combine 0.4 gm of A. simplex cells 50 ml of 50 mM KPO$_4$ buffer, pH=7.5

Agitate for 2 hours or until uniform slurry is obtained.

Take 2–25 ml fractions and add to 125 ml flasks.

Add to each flask 0.25 ml of 5 mM menadione in 3A-alcohol 0.2 gm of androsta-4,9(11) diene-3,17-dione.

Add 2 ml of toluene to one of the stoppered flasks and Agitate on wrist action shaker for 4 days.

After 4 days extract with 25 ml of toluene.

Analyze extracts.

(B) Results:

|  | Procedure | |
|---|---|---|
|  | Aqueous | Toluene |
| (Substrate) | | |
| Androstra-4,9(11)diene-3,17-dione | 17.7% | 0.00% |
| (Product) | | |
| Androstra-1,4,9(11)triene-3,17-dione | 82.3% | 100.00% |

EXAMPLE 3

The following steroidal compounds were exposed to dried cells of A. simplex in accordance with the conditions described in Example 1 in order to obtain the corresponding 1,2-dehydro derivatives:

| No. | Name |
|---|---|
| 1. | androsta-4-ene-3,17-dione |
| 2. | 6$\alpha$-fluoro-androsta-4,9(11)-diene-3,17-dione |
| 3. | 6$\alpha$-methyl-androsta-4,9(11)-diene-3,17-dione |
| 4. | 16$\beta$-methyl-androsta-4,9(11)-diene-3,17-dione |
| 5. | 17$\alpha$-hydroxypregn-4-ene-20-yn-3-one |
| 6. | 17$\alpha$-hydroxypregn-4,9(11)-diene-20-yn-3-one |
| 7. | 17$\alpha$-hydroxy-16$\beta$-methyl-pregn-4,9(11)-diene-20-yn-3-one |
| 8. | 21-acetoxy-11$\beta$-hydroxy-pregn-4,17(20)-diene-3-one |
| 9. | 20-chloro-pregn-4,9(11),17(20)-triene-21-al-3-one |
| 10. | 21-acetoxy-17-hydroxy-pregn-4,9(11)-diene-3,20-dione |
| 11. | 21-acetoxy-17-hydroxy-16$\alpha$-methyl-pregn-4,9(11)-diene-3,20-dione |
| 12. | 21-benzoyloxy-17-hydroxy-16$\beta$-methyl-pregn-4,9(11)-diene-3,20-dione |
| 13. | 21-acetoxy-17-hydroxy-16$\beta$-methyl-pregn-4,9(11)-diene-3,20-dione |
| 14. | 21-acetoxy-pregn-4,9(11),16-triene-3,20-dione |
| 15. | 21-acetoxy-6$\alpha$-fluoro-pregn-4,9(11),16(17)-triene-3,20-dione. |

The corresponding products obtained from the conversions are as follows:

| No. | Products |
|---|---|
| 1a | androsta-1,4-diene-3,17-dione |
| 2a | 6$\alpha$-fluoro-androsta-1,4,9(11)-triene-3,17-dione |
| 3a | 6$\alpha$-methyl-androsta-1,4,9(11)-triene-3,17-dione |
| 4a | 16$\beta$-methyl-androsta-1,4,9(11)-triene-3,17-dione |
| 5a | 17$\alpha$-hydroxypregn-1,4-diene-20-yn-3-one |
| 6a | 17$\alpha$-hydroxypregn-1,4,9(11)-triene-20-yn-3-one |
| 7a | 17$\alpha$-hydroxy-16$\beta$-methyl-pregn-1,4,9(11)-triene-20-yn-3-one |
| 8a | 21-acetoxy-11$\beta$-hydroxy-pregn-1,4,17(20)-triene-3- |

-continued

| No. | Products |
|---|---|
|  | one and |
|  | 11β,21-dihydroxy-pregn-1,4,17(20)-triene-3-one |
| 9a | 20-chloro-pregn-1,4,9(11),17(20)-tetraene-21-al-3-one |
| 10a | 21-acetoxy-17-hydroxy-pregn-1,4,9(11)-triene-3,20-dione and 17,21-dihydroxy-pregn-1,4,9(11)-triene-3,20-dione |
| 11a | 21-acetoxy-17-hydroxy-16α-methyl-pregn-1,4,9(11)-triene-3,20-dione and 17,21-dihydroxy-16α-methyl-pregn-1,4,9(11)-triene-3,20-dione |
| 12a | 21-benzoyloxy-17-hydroxy-16β-methyl-pregn-1,4,9(11)-triene-3,20-dione |
| 13a | 21-acetoxy-17-hydroxy-16β-methyl-pregn-1,4,9(11)-triene-3,20-dione and 17,21-dihydroxy-16β-methyl-pregn-1,4,9(11)-triene-3,20-dione |
| 14a | 21-acetoxy-pregn-1,4,9(11),16-tetraene-3,20-dione and 21-hydroxy-pregn-1,4,9(11),16-tetraene-3,20-dione |
| 15a | 21-acetoxy-6α-fluoro-pregn-1,4,9(11),16-tetraene-3,20-dione and 6α-fluoro-21-hydroxy-pregn-1,4,9(11),16-tetraene-3,20-dione. |

I claim:

1. A process for converting a 1,2-saturated steroid to a 1,2-dehydro steroid which comprises contacting the 1,2-saturated steroid with *Arthrobacter simplex* or *Bacterium cyclooxydans* in the presence of an exogenous electron carrier, a water-immiscible aromatic hydrocarbon solvent where the oxygen concentration is maintained below the minimum oxygen concentration required for combustion or where the reaction is performed below the flash point of the mixture with the proviso that the 1,2-saturated steroid has a solubility in the water-immiscible aromatic hydrocarbon solvent of greater than 5 g/liter.

2. A process according to claim 1 where the water-immiscible aromatic hydrocarbon solvent is present in an amount one-half of which is necessary to dissolve the most soluble of the 1,2-saturated steroid substrate or 1,2-dehydro steroid product to about four times the amount which is necessary to dissolve the least soluble of the 1,2-saturated steroid substrate or 1,2-dehydro steroid product.

3. A process according to claim 1 where the exogenous electron carrier is selected from the group consisting of menadione, menadione bisulfite, 1,4-naphthoquinone, or other vitamin K-type compounds.

4. A process according to claim 1 where the water-immiscible aromatic hydrocarbon solvent is selected from the group consisting of benzene, toluene, and xylene.

5. A process according to claim 1 where the 1,2-saturated steroid is selected from the group consisting of androstene or pregnene steroids.

6. A process according to claim 1 where the water-immiscible aromatic hydrocarbon solvent can be diluted with another water-immiscible solvent such as the group consisting of heptane or methylene chloride.

7. A process according to claim 1 where the 1,2-saturated steroid is selected from the group consisting of androst-4-ene-3,17-dione, 6α-fluoroandrosta-4,9(11)-diene-3,17-dione, 6α-methylandrosta-4,9(11)-diene-3,17-dione, 16β-methylandrosta-4,9(11)-diene-3,17-dione, 17α-hydroxypregn-4-ene-20-yn-3-one, 17α-hydroxypregna-4,9(11)-diene-20-yn-3-one, 17α-hydroxy-16β-methylpregna-4,9(11)-diene-20-yn-3-one, 21-acetoxy-11β-hydroxypregna-4,17(20)-dien-3-one, 20-chloropregna-4,9(11),17(20)-trien-21-al-3-one, 21-acetoxy-17-hydroxypregna-4,9(11)-diene-3,20-dione, 21-acetoxy-17-hydroxy-16α-methylpregna-4,9(11)-diene-3,20-dione, 21-benzoyloxy-17-hydroxy-16β-methylpregna-4,9(11)-diene-3,20-dione, 21-acetoxy-17-hydroxy-16β-methylpregna-4,9(11)-diene-3,20-dione, 21-acetoxypregna-4,9(11),16-triene-3,20-dione, 21-acetoxy-6α-fluoropregna-4,9(11),16-triene-3,20-dione or androsta-4,9(11)-diene-3,20-dione.

8. A process according to claim 1 where the 1,2-saturated steroid is selected from the group consisting of androst-4-ene-3,17-dione, 16β-methylandrosta-4,9(11)-diene-3,17-dione, 21-acetoxypregna-4,9(11),16-triene-3,20-dione, 21-acetoxy-6α-fluoropregna-4,9(11),16-triene-3,20-dione and androsta-4,9(11)-diene-3,20-dione.

9. A process according to claim 1 where the microorganism is *Arthrobacter simplex*.

* * * * *